United States Patent [19]

Ray

[11] Patent Number: 4,805,599
[45] Date of Patent: Feb. 21, 1989

[54] FRAMEWORK FOR SUPPORTING SURGICAL INSTRUMENTS AT A SURGICAL WOUND

[75] Inventor: Charles D. Ray, Wayzata, Minn.

[73] Assignee: Cedar Surgical, Inc., Minnetonka, Minn.

[21] Appl. No.: 66,147

[22] Filed: Jun. 25, 1987

[51] Int. Cl.⁴ .................. A61B 17/02; A61F 13/00; A61G 13/00
[52] U.S. Cl. .................................... 128/2; 128/869; 269/328
[58] Field of Search .............. 128/20, 68, 70, 78, 128/133, 134; 269/322–328

[56] References Cited

U.S. PATENT DOCUMENTS

| | | | |
|---|---|---|---|
| 1,230,873 | 6/1917 | Crossley | 128/20 |
| 2,586,488 | 2/1952 | Smith | 128/20 |
| 2,594,086 | 4/1952 | Smith | 128/20 |
| 3,040,739 | 6/1962 | Grieshaber | 128/20 |
| 3,221,743 | 8/1962 | Thompson et al. | 128/20 |
| 3,522,799 | 8/1970 | Gauthier | 128/20 |
| 3,572,326 | 5/1968 | Jensen | 128/20 |
| 3,970,075 | 7/1976 | Sindelar et al. | 128/20 |
| 4,254,763 | 3/1981 | McCready et al. | 128/20 |
| 4,355,631 | 10/1982 | LeVahn | 128/20 |
| 4,380,999 | 4/1983 | Healy | 128/20 |
| 4,391,438 | 7/1983 | Heffihgton | 269/328 |
| 4,481,943 | 11/1984 | Michelson | 269/328 |
| 4,617,916 | 10/1986 | LeVahn et al. | 128/20 |
| 4,662,619 | 5/1987 | Ray et al. | 269/328 |

FOREIGN PATENT DOCUMENTS 2556588 6/1985 France ...................... 269/328

*Primary Examiner*—Richard C. Pinkham
*Assistant Examiner*—Mark S. Graham
*Attorney, Agent, or Firm*—Moore & Hansen

[57] ABSTRACT

For use in back surgery, a known kneeling attachment to an operating table has a platform on which a patient kneels with the torso positioned over one end of an operating table and the buttocks resting against the padded crosspiece of a rigid U-shaped yoke. The invention concerns a substantially rectangular rigid frame which can be mounted on the yoke with an outboard crossarm of the frame attached to the crosspiece of the yoke and the inboard end of the frame attached to the arms of the yoke. The frame is useful for supporting surgical instruments such as retractors at a surgical wound, in particular a retraction device that a surgeon can adjust with one hand, even without looking. The frame also makes possible a new surgical procedure by which a dislocated vertebra can be moved into position by a lifting mechanism suspended from the frame.

10 Claims, 5 Drawing Sheets

FRAMEWORK FOR SUPPORTING SURGICAL INSTRUMENTS AT A SURGICAL WOUND

CROSS-REFERENCE TO COPENDING APPLICATION

The framework of this invention can be mounted on the buttocks support disclosed and claimed in an application entitled "Retractable Buttocks Support for Operations in the Prone Sitting Position" (Attorney Docket R-13) Ser. No. 07/158,149 filed of even date herewith and assigned to the company to which this invention is assigned. The disclosure of that application is incorporated here by reference.

BACKGROUND OF THE INVENTION

1. Field of the Invention

The invention relates to a framework useful for supporting surgical instruments such as retractors at a surgical wound. The framework of the invention can be used during back surgery in conjunction with a kneeling attachment including a platform on which a patient kneels with the torso positioned over one end of an operating table while the buttocks rest against a buttocks support. The novel framework can also be used during back surgery on a prone, face-down patient. The invention also concerns both a retraction device and a surgical procedure for realigning vertebrae.

2. Description of Related Art

U.S. Pat. No. 4,254,763 (McCready et al.) reports that "in surgical operations on the chest or abdomen, it is customary to employ a retraction apparatus. Most, if not all, versions of the retraction apparatus are attached directly to the operating room table by means of affixation to a rail which is provided along each side of the table. Whether by connection to one or both rails, the retraction apparatus generally provides a framework extending over the region of the patient in which the operation is to be performed. One or more retractor blades are attached to the framework, and these blades are positioned in the incision and serve to hold back tissue, organs, and the like so that the surgeon may operate on the intended area" (col. 1, lines 11-27). While the McCready framework includes a rig-like frame from which retractors are suspended, a number of patents show rectangular frames. See, for example, U.S. Pat. Nos. 3,522,799 (Gauthier), 3,221,743 (Thompson et al.), 3,572,326 (Jensen), and 4,355,631 (LeVahn). Other U.S. patents showing ring-like frames include U.S. Pat. Nos. 2,586,488 (Smith), 2,594,086 (Smith), and 3,040,739 (Grieshaber). A frame of different shape is shown in U.S. Pat. No. 4,617,916 (LeVahn et al.). The framework of each of these patents is supported by siderails of the operating table, except that we fail to find in Gauthier any mention of support for his framework.

Apparatus like that shown in the LeVahn et al. patent is sold for use in abdominal surgery as the Omni-Tract 3005 Upper Abdominal/Bariatric Retractor System by Minnesota Scientific, Inc., Minneapolis, MN. The Omni-Tract framework includes a "crossbar" that is clamped by one or two posts to one or both rails of an operating table. Universal joints at the top of each of the posts permit the crossbar to be adjusted to the desired height and lateral distance from the surgical wound. Retractors can be mounted on the crossbar using universal clamps which can be swiveled to provide the desired lateral retraction from positions that do not obstruct access to the wound.

Because of the far greater force needed to retract the powerful muscles of the back, the above-discussed frameworks are not said to be useful for back surgery. Furthermore, it is believed that no framework is available that would be suitable for supporting retractors above a surgical wound in the back. Instead of using such a framework, it is quite common in back surgery for a surgical assistant to hold a Hibbs-type retractor in place manually, sometimes for several hours. Not only does this fully occupy the assistant, but there is a danger that the assistant could move the retractor in a hazardous manner, and the danger could be amplified due both to fatigue and to boredom.

For back surgery, especially involving the lumber spine, an operating table may be fitted with a kneeling attachment that permits a patient to assume the prone sitting position with the torso positioned over one end of the table. The buttocks can rest against a padded seat carried by the crosspiece of a rigid U-shaped yoke, the ends of which are releasably locked to opposite sides of the operating table. See, for example, U.S. Pat. No. 4,662,619 (Ray et al.); U.S. Pat. No. 4,391,438 (Heffington); and a brochure entitled "Andrews Spinal Surgery Frame" of Orthopedic Systems, Inc., Hayward, California. In using the kneeling attachment of the Ray et al. patent, the upper torso preferably rests on a cushion of sufficient height that the patient's arms can be comfortably tucked under the stomach.

SUMMARY OF THE INVENTION

The invention provides a framework useful for supporting surgical instruments such as retractors at a surgical wound during back surgery on a patient in a kneeling or prone sitting position, the framework being adapted to be so supported as to be capable of accommodating forces required to retract the powerful muscles of the back. As compared to frameworks shown in the above-cited patents, a preferred framework of the invention is remarkably uncluttered, easy to keep clean, and economical to manufacture. Even though some figures of the appended drawing show it beneath surgical drapery, the framework preferably is mounted over the drapery, permitting the framework to be removed and reattached without disturbing the drapery.

The framework of the invention is particularly useful in back surgery using a kneeling attachment including a platform on which a patient kneels with the torso positioned over one end of an operating table and the buttocks resting against the crosspiece of a rigid U-shaped yoke. Briefly, the novel framework includes:

a substantially rectangular rigid frame including two substantially parallel legs, the ends of which are interconnected by first and second crossarms that extend substantially orthogonally to the legs and are shorter than the legs, and means for releasably attaching the first or outboard crossarm to the crosspiece of said yoke and for attaching the frame near each end of the second or inboard crossarm to the platform with the legs of the frame extending over the bed of the operating table substantially parallel to its sides.

Said means for attaching the frame near the ends of the inboard crossarm can connect either directly to the platform or indirectly by being attached to the arms of the U-shaped yoke.

The novel framework is believed to be the first to be useful in back surgery on a kneeling patient to replace a surgical assistant by holding a retractor at the proper angle in a surgical wound.

While being designed primarily for use with a kneeling patient, the substantially rectangular frame of the novel framework can also be used with a prone, face-down patient by equipping it with means for attaching it directly to an operating table, e.g., to its siderails.

In the rigid frame of the novel framework, each of the crossarms preferably is centrally disconnectable to separate the frame into two substantially equal pieces which fit more easily into autoclaves than would a unitary frame.

Preferably, the inboard crossarm of the frame of the novel framework is arched out of the plane defined by the legs of the frame and away from the bed of an operating table to which the frame is attached. This allows the legs of the frame to be approximately at the level of the patient's back while avoiding any contact between the frame and the back of the patient's chest. If it were necessary for the legs to be higher with respect to the patient's back, the frame might unduly interfere with access by the surgeon to the wound. When the legs of the frame are approximately level with the patient's back and hence above the bony anatomy (i.e., the spinous processes, vertebrae, etc.), they can be metal and yet not obstruct lateral x-rays.

In order to suspend surgical instruments from directly above the wound, the novel framework may include a rigid crossbar that can be connected across the legs of the frame. Such a crossbar is particularly useful for positioning a variety of surgical accessories other than retractors, e.g., bone clamps, x-ray markers, bone drill systems, and bone screw inserting devices. This also makes possible an important new surgical procedure by which a dislocated vertebra can be moved into position by a lifting mechanism such as a screw suspended either from the crossbar or from another rigid bar connected across two such crossbars.

The novel buttocks support preferably is used in conjunction with a kneeling attachment which has a platform made of radiotransparent materials. This permits x-ray beams to pass from a generator positioned beneath the platform, through the front of the patient's body, and to an image tube positioned above the patient's back. Since the lumbar spine may now be operated upon in the kneeling position, yet under full biplane x-ray visualization, guided surgical procedures on the lumbar spine may be performed that have previously been impossible.

The frame of the novel framework by itself preferably forms a complete rectangle, but it can form an open-ended U that becomes a complete rectangle only when attached to the crosspiece of the yoke that supports the kneeling patient's buttocks. Usually a padded seat is fastened to the crosspiece, in which event the open-ended U can be converted into a complete rectangle either by the crosspiece itself or by a rigid seat plate. The frame is less likely to be damaged accidentally when it forms a complete rectangle before being attached.

THE DRAWING

The invention will be more easily understood in reference to the drawing, all figures of which are schematic, wherein.

Figure 1:
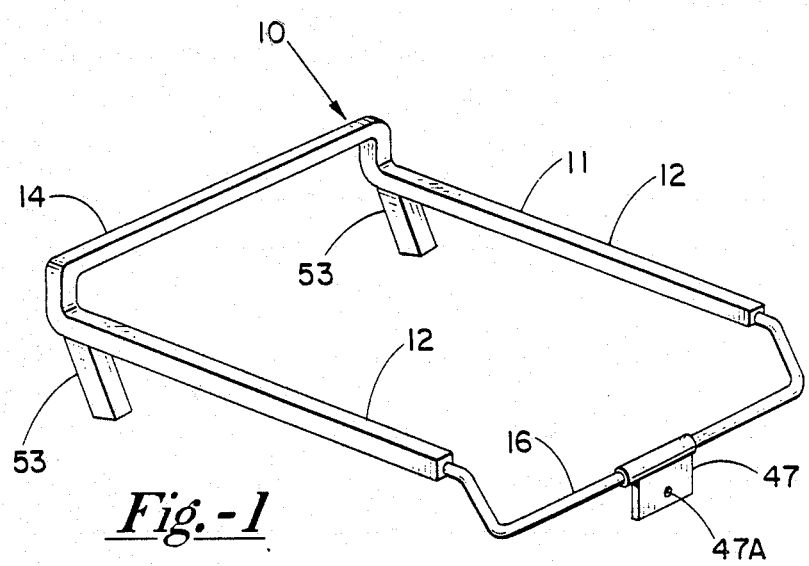
FIG. 1 is a perspective view of a framework of the invention.
Figure 2:
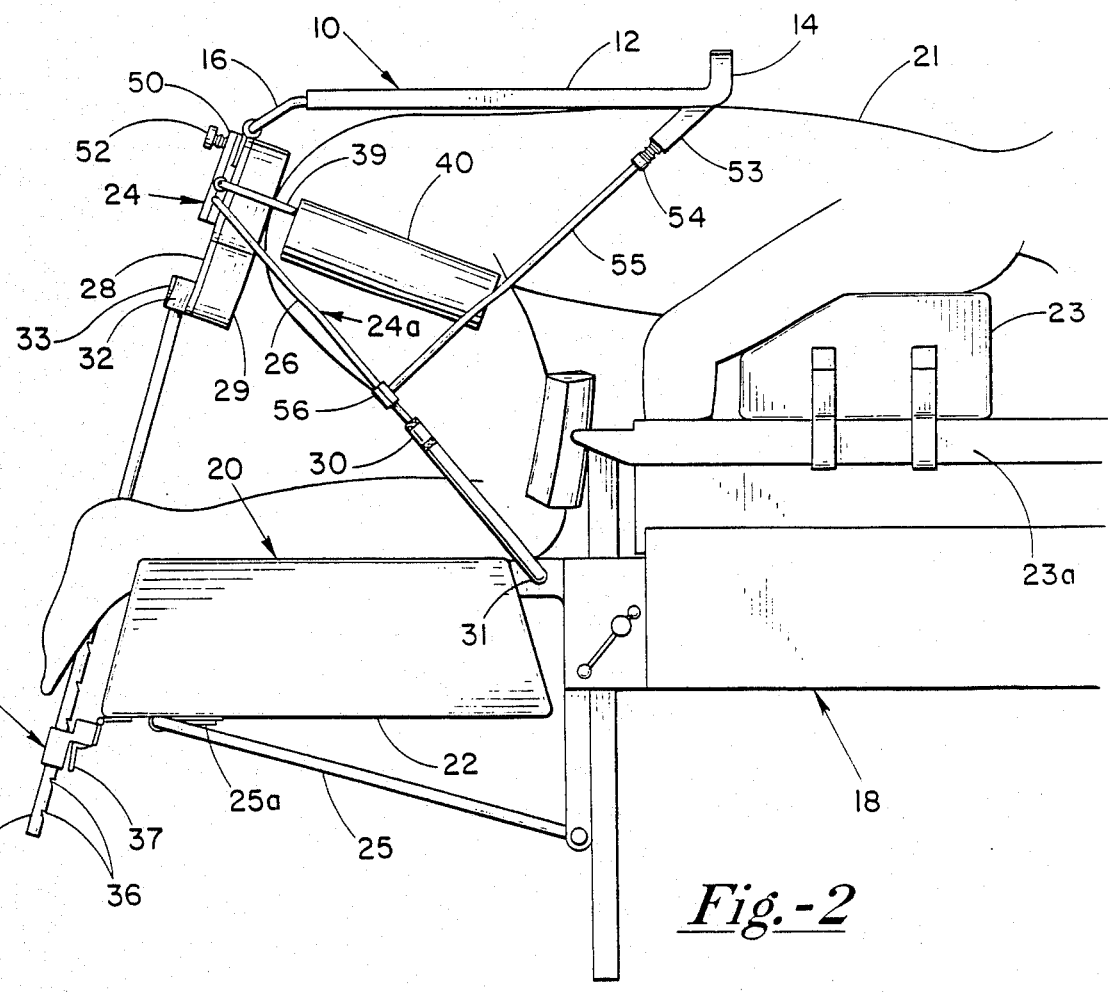
FIG. 2 is a plan view of the framework of FIG. 1 mounted on a buttocks support of a kneeling attachment to an operating table.

The framework shown in FIGS. 1 and 2 includes a unitary, substantially rectangular rigid frame 10 provided by a metal rod 11 that forms a complete rectangle having two relatively long parallel legs 12, the ends of which are interconnected by an arched inboard second crossarm 14 and an outboard first crossarm 16 which are shorter than the legs. In FIG. 2, the rigid frame 10 is shown attached to an operating table 18 having a kneeling attachment 20 permitting a patient 21 to kneel on a platform 22 with the torso positioned over one end of the operating table and resting on a torso cushion 23 which is strapped to the siderails 23a of the operating table 18. The patient's buttocks rest against a buttocks support 24. As taught in the Ray et al. patent, the platform can either be supported from the floor by a post 25 or can be locked to move up and down with the operating table while the post 25 is retracted and held by a Velcro strap 25a as in FIG. 2.

Figure 3:
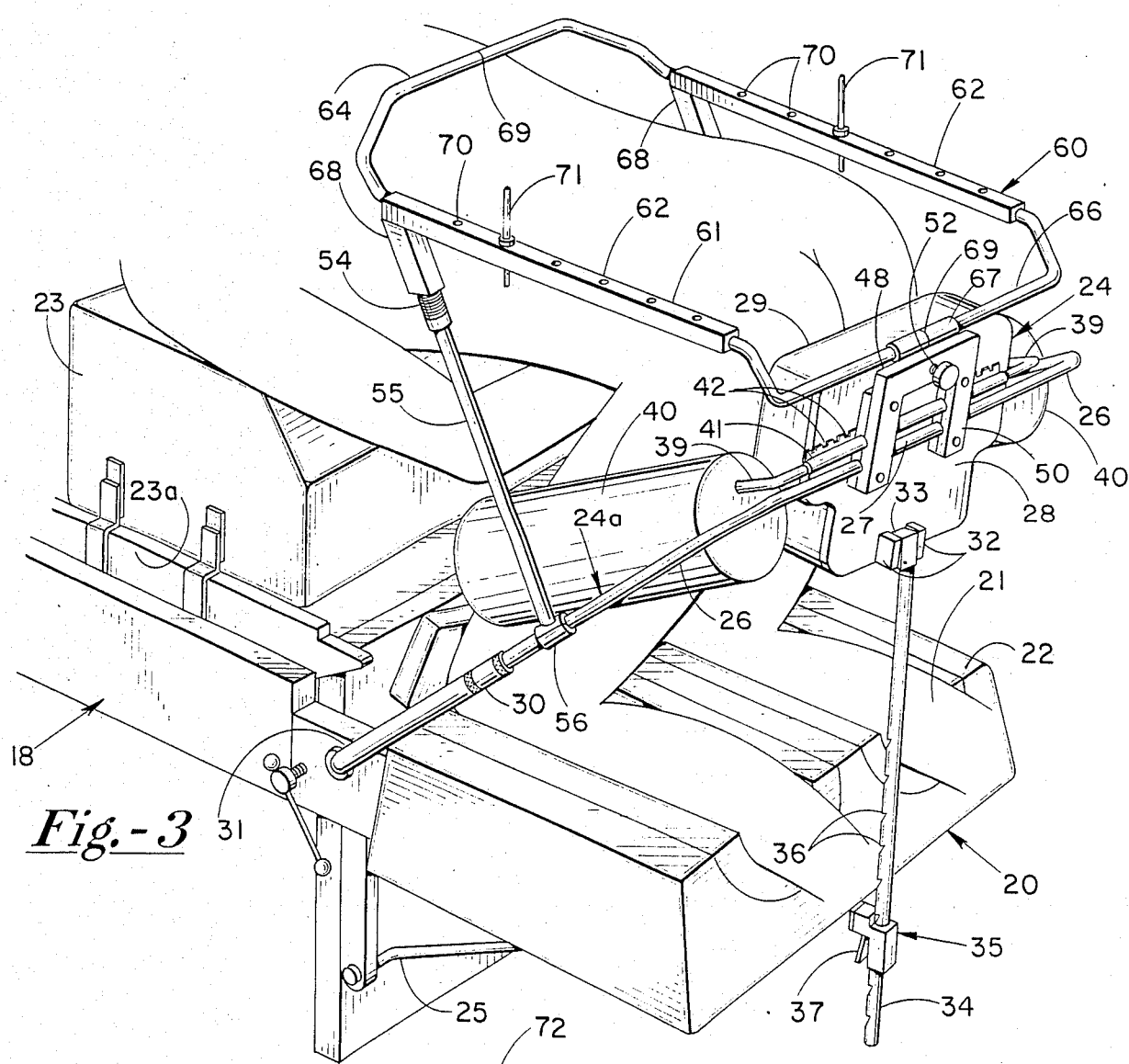
FIG. 3 is a perspective view of another framework of the invention mounted on a buttocks support of a kneeling attachment to an operating table.

The buttocks support 24 includes a metal U-shaped yoke 24a having two arms 26 and a crosspiece 27 (shown in FIG. 3). Pivotably mounted on the crosspiece is a rigid seatplate 28, on the face of which is a buttocks cushion 29. The arms 26 of the yoke telescope at a friction lock 30 and are pivotably attached at 31 to the inboard end of the platform 22.

Pivotably mounted between two plates 32 bolted to the back of the seatplate 28 is a block 33 that is fixed to the upper end of a metal mast 34, the lower end of which is telescopically connected to the outboard end of the platform 22 by a ratchet assembly 35. Formed in the inner facig surface of the mast 34 are notches 36 into which fit a spring-loaded lever 37 (spring not shown) that can be manually retracted to lower the mast.

Pivotably and slidably positionable at the back of the seatplate 21 is each of a pair of metal L-shaped rods 39. A first arm of each of the rods fits snugly into an off-center bore of a cylindrical thigh-supporting cushion 40. Welded to the second arm of each of the rods is a bracket 41 that is formed with notches 42 into which fits a pin (not shown) protruding from the back of the seatplate 28. When an attendant lifts a thigh-supporting cushion 40, the bracket 41 is moved away from the pin, thus permitting the attendant to slide the second arm of the L-shaped rod 39 in the direction of the crosspiece 27 until its thigh-supporting cushion fits snugly against a patient's thigh, and then to push the cushion downwardly until the pin fits into another notch 42.

At the center of the outboard crossarm 16 of the frame 10 is a hinge 47 having a tang that fits into a slot 48 between the back of the seatplate 21 and a split bracket 50 that is bolted to the seatplate. When the tang of the hinge 47 is inserted into the slot as shown in FIG. 2, a knob 52 that is threaded into the under half of the split bracket 50 is tightened into a seat 47A in the tang of the hinge to lock the outboard crossarm of the frame 10 to the buttocks support 24.

Welded to the inboard end of each of the legs 12 of the frame 10 is a stub 53, into which is threaded a collar 54 at the end of a shaft 55. The other end of the shaft is attached by a split clamp 56 to one of the arms 26 of the U-shaped yoke 24a. The threaded collars permit the frame 10 to be raised or lowered, but the frame should never be lowered to the extent that there is any danger of the inboard crossarm 14 coming into contact with the back of the patient's chest. The inboard crossarm 14 is arched upwardly to minimize any such danger.

The frame 10 should be mounted on the buttocks support 24 after the patient has been covered by surgical drapery. This enables the frame to be removed more quickly should there be an emergency requiring that the patient be turned face-up. It also permits the frame to be removed and reattached without disturbing the drapery. After the drapery has been pushed into the slot 48 by the tang of the hinge 47, it would be awkward to tighten the knob 52 by twisting it through the drapery. Hence, it would be preferred to employ some other means for clamping the tang of the hinge into the slot 48. For example, the tang can be clamped by a toggle actuated by moving a lever that is inside the drapery but can be pushed from the outside of the drapery. Another means employs a hinge having a split tang which expands in the slot 48 by turning a screw that is outside of the drapery.

The framework shown in FIG. 3 is used with the same operating table 18, kneeling attachment 20, and buttocks support 24 as are shown in FIGS. 1 and 2. The framework of FIG. 3 includes a substantially rectangular rigid frame 60 formed from a metal rod 61 to have long parallel legs 62, the ends of which are interconnected by an arched inboard crossarm 64 and an outboard crossarm 66. At the center of the outboard crossarm 66 is a hinge 67 having a tang that is locked to the buttocks support 24 in the same manner as is the hinge 47 of the frame 10 of FIGS. 1 and 2. Extending downwardly from the legs 62 near the ends of the inboard crossarm 64 are internally threaded stubs 68 which permit the frame 60 to be mounted on the buttocks support 24 in the same manner as in the frame 10 of FIGS. 1 and 2.

The metal rod 61 is formed in two pieces, each of which is unitary both for strength and for ease of being kept clean. The ends of one of the pieces fit into the the ends of the other at the center 69 of each of the inboard second and outboard first crossarms 64,66. By disconnecting the two unitary pieces and the shafts 55, all four parts will fit into a conventional autoclave for sterilization. Formed in each of the legs 62 is a series of cylindrical openings 70 for receiving posts 71 to which surgical retractors or other instruments can be releasably attached.

Figure 4:
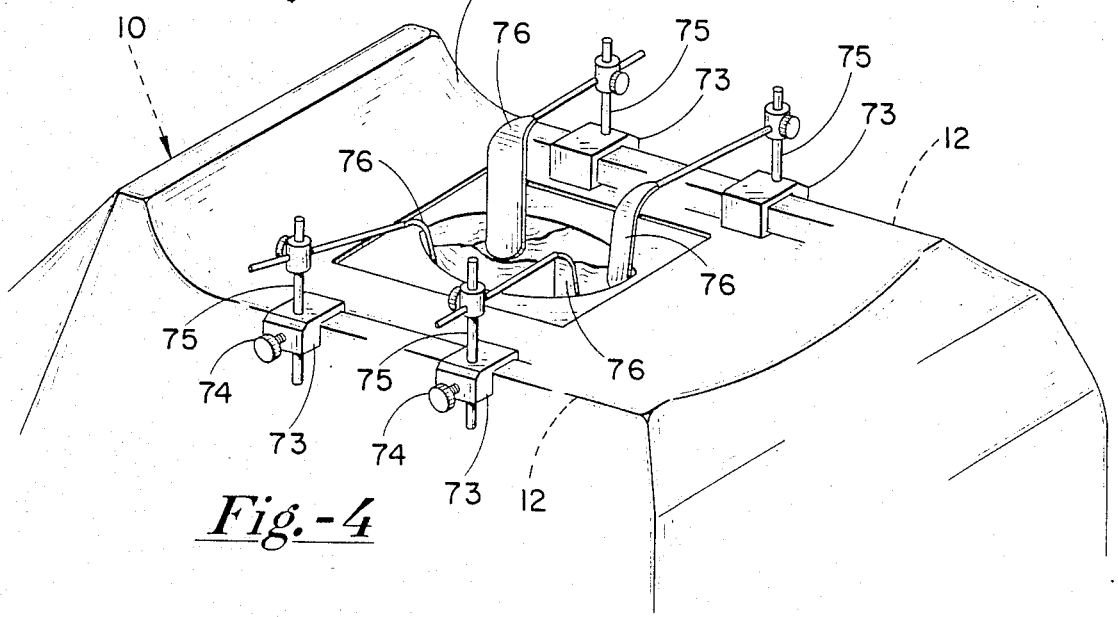
FIG. 4 is a perspective view of the framework of FIG. 1 with which a number of retractors are positioned in a surgical wound.

In FIG. 4, the frame 10, while supported as shown in FIG. 2, has been covered by a surgical drape 72 over a kneeling patient. Fitting onto the legs 12 over the drape are four slides 73, each locked in place by a setscrew 74. Each slide carries an upstanding post 75 to which is clamped a surgical retractor 76. Any force applied laterally to one of the retractors 76 is counterbalanced by the thigh-supporting cushion 40 at the opposite side of the buttocks support 24, so that the patient is not moved out of position by the applied force.

Figure 5:
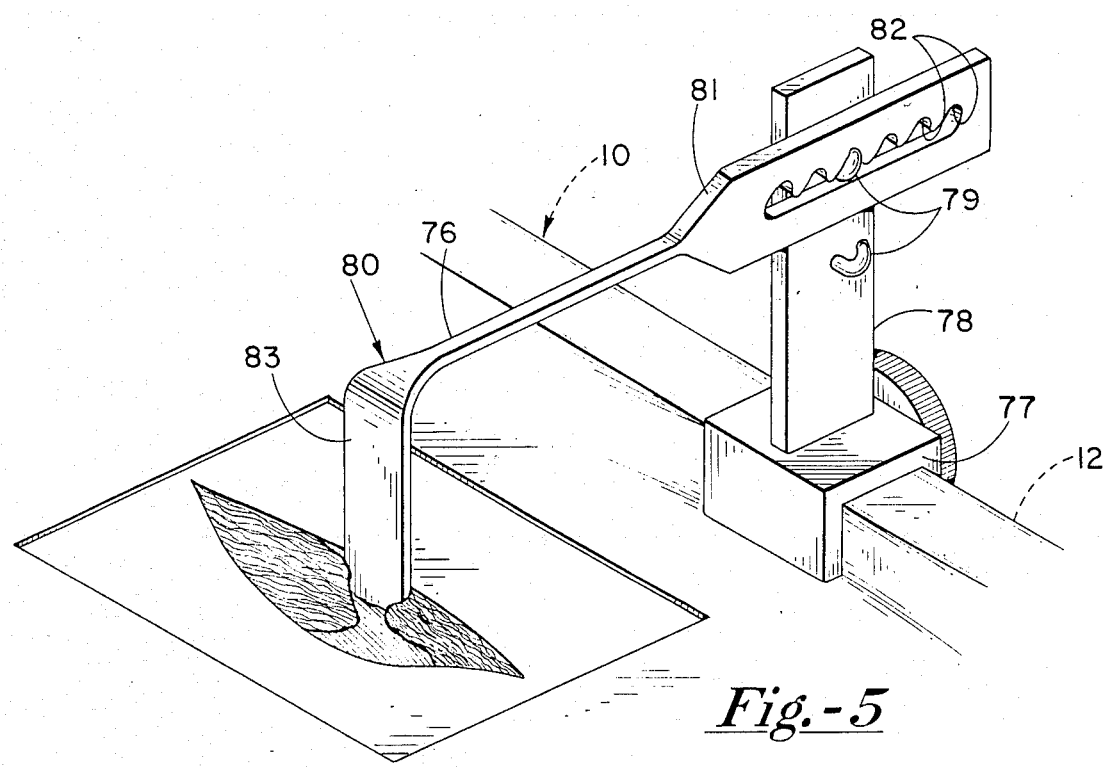
FIG. 5 is a perspective view showing a fragment of the framework of FIG. 1 to which is attached a retraction device that a surgeon can adjust with one hand.

In FIG. 5, locked to a leg 12 of the frame is a slide 77 carrying an upstanding rectangular post 78, from each broad side of which projects two hooks 79. A surgical retractor 80 has an arm 81 formed with a ratchet 82 that rests on an upper of the hooks 79 and is held by gravity and by elastic recoil of the tissue to maintain the traction applied when the surgeon set the blade 83 of the retractor in the wound.

Figure 6:
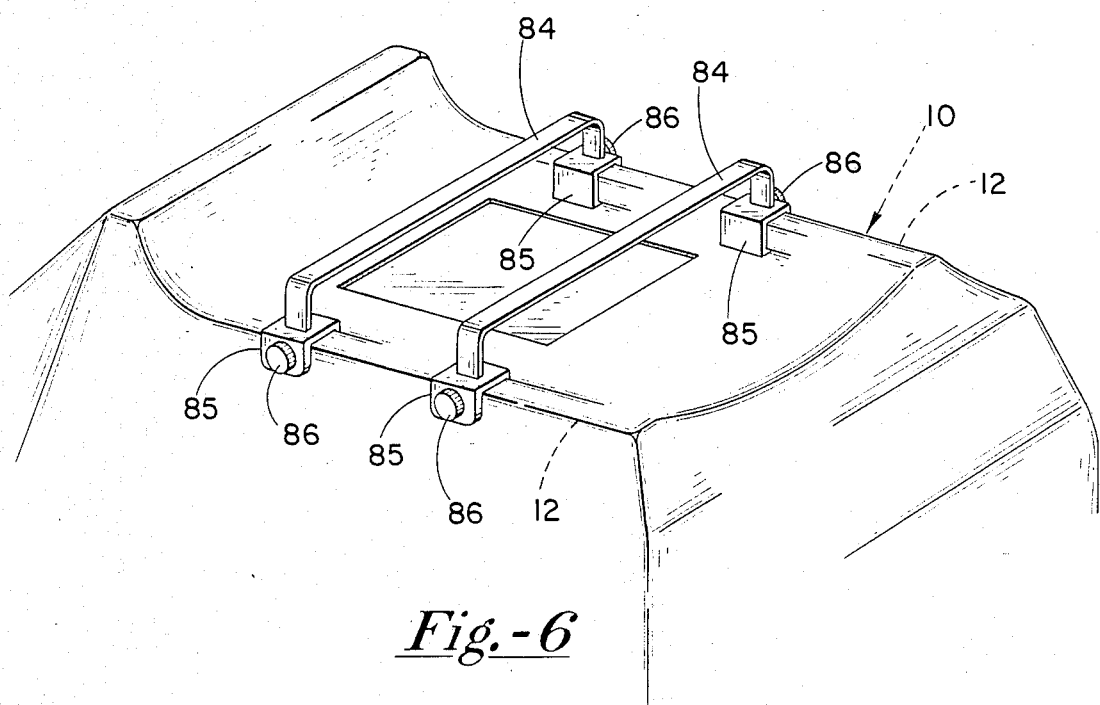
FIG. 6 is a perspective view showing the framework of FIG. 1 bearing a pair of rigid crossbars.

In FIG. 6 with the substantially rectangular frame 10 covered by a surgical drape, each of a pair of rigid crossbars 84 is secured by a pair of slides 85 across the legs 12 of the frame, and each slide is locked in place by a setscrew 86.

Figure 7:
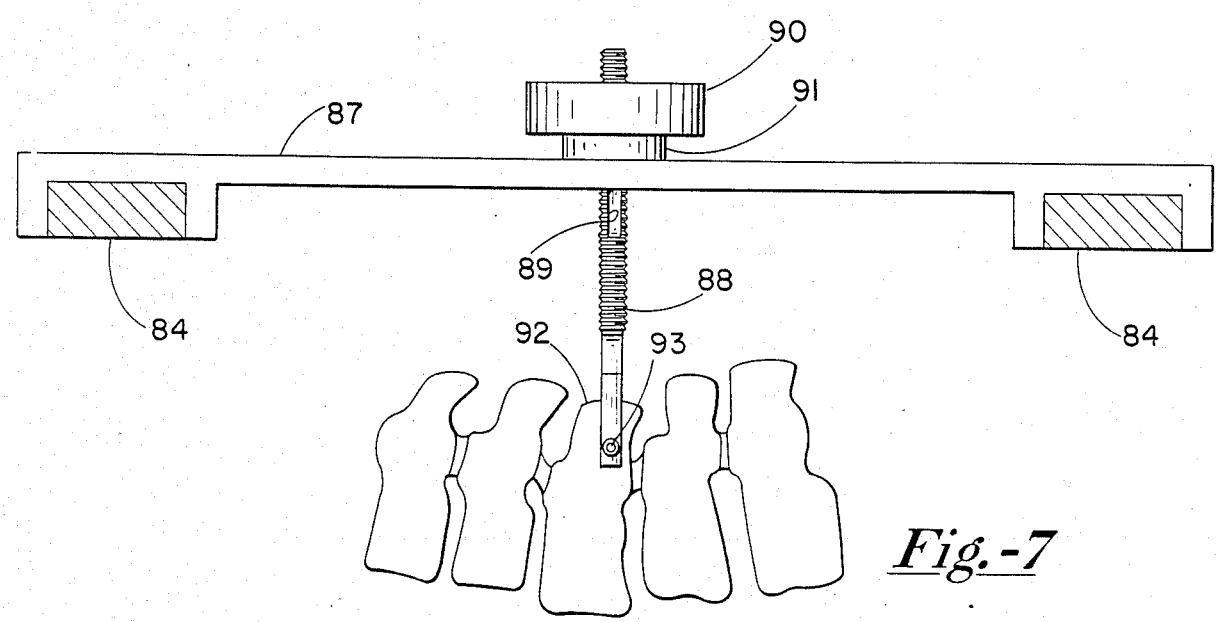
FIG. 7 is a plan view showing the use of the rigid crossbars of FIG. 6 in a surgical procedure by which a dislocated vertebra can be moved into position.

In FIG. 7, a rigid bar 87 rests across the pair of crossbars 84 of FIG. 6 that are attached to the legs of the frame 10. Slidably received in a cylindrical opening through in the center of the bar 87 is a screw 88 which is formed with a slot 89 that fits into a key (not shown) in the cylindrical opening to prevent the screw from rotating. The screw 88 mates with a knurled nut 90 that is spaced from the bar by a washer 91. A dislocated vertebra 92 has been drilled to receive a pin 93 by which the vertebra is releasably fastened to the bifurcated end of the screw 88. Rotation of the nut 90 will lift the dislocated vertebra into alignment. During this procedure, it may be desirable to suspend other clamps (not shown) from one or more of the crossbars 84, bar 87, legs 12, and crossarms 14,16 in order to hold the other parts of the spine in alignment.

Figure 8:
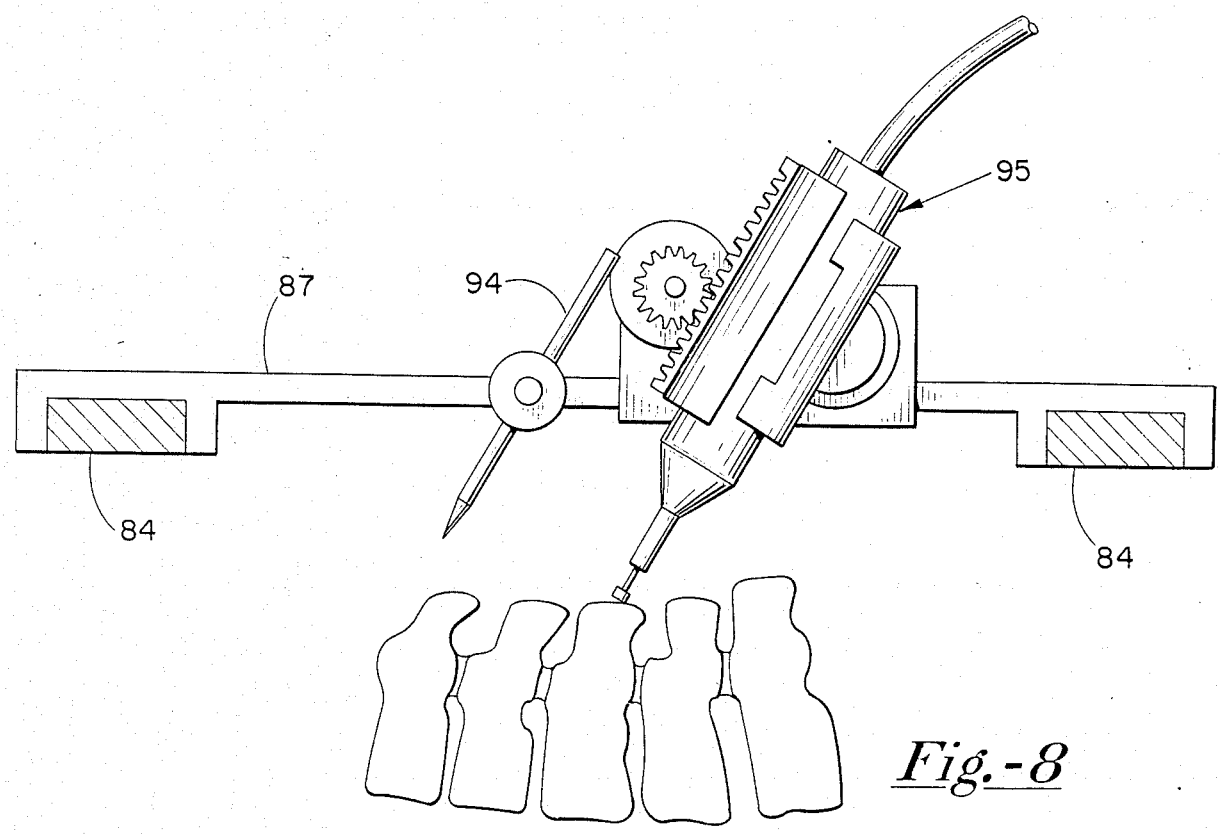
FIG. 8 is a plan view showing two surgical instruments suspended above a surgical wound using the rigid crossbars of FIG. 6.

In FIG. 8, the rigid bar 87 of FIG. 7 is used to position a pointer 94 and a drill 95 above a patient's backbone. After using the pointer to determine the exact location and angle at which a hole is to be drilled in a vertebra, the drill is moved along the bar 87 to the identical position and angle and held securely while the hole is drilled.

Figure 9:
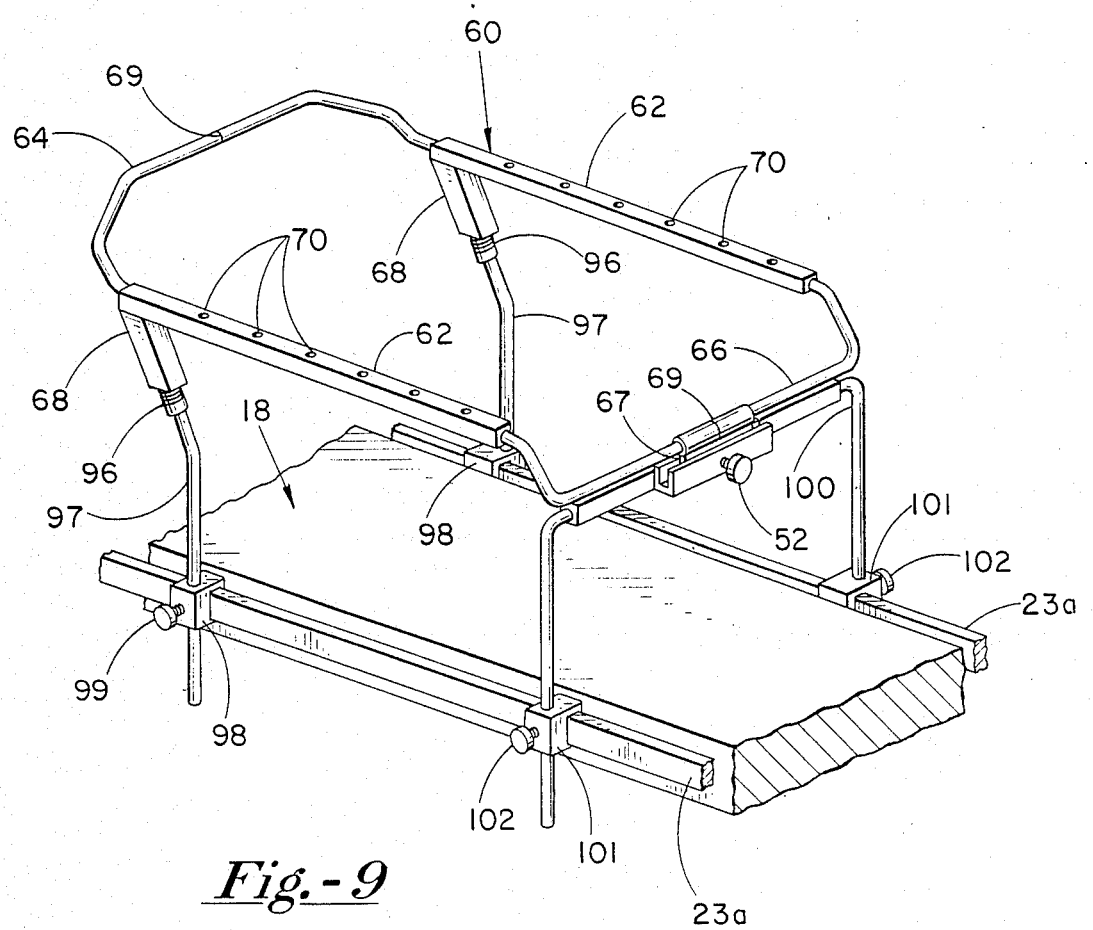
FIG. 9 is a perspective view showing means for attaching the framework of FIG. 3 to the siderails of an operating table.

FIG. 9 shows how the substantially rectangular frame 60 of FIG. 3 can be fitted to be fastened to the operating table 18 for use at a surgical wound in the back of a prone, face-down patient. Screwed onto each of the stubs 68 is a threaded collar 96 at one end of a support 97, the other end of which is secured to a slide 98 that can be locked with a knob 99 to a siderail 23a of the operating table 18. The tang of the hinge 67 at the center of the outboard crossarm 66 is clamped onto an arch 100, each end of which is secured to a slide 101 having a knob 102 by which it can be locked to one of the siderails.

EXAMPLE

A prototype of the frame 60 of FIG. 3 has been made from stainless steel to the following dimensions:

Thickness of legs 62 1.6 cm square
Overall length 60 cm
Overall width 40 cm
Diameter of openings 54 0.64 cm
Rise of arc of inboard crossarm 44 7.8 cm
I claim:

1. Framework useful for supporting surgical instruments such as retractors at a surgical wound during back surgery in conjunction with a kneeling attachment, said framework comprising:
   a platform,
   means for attaching the platform to an operating table to permit a patient to kneel on the platform with the torso positioned over one end of an operating table,
   a rigid U-shaped yoke,
   means for releasably supporting the yoke from the operating table to permit the buttocks of a kneeling patient to be supported by the crosspiece of the yoke,
   a substantially rectangular rigid frame including two substantially parallel legs, the ends of which are interconnected by first and second crossarms that extend substantially orthogonally to the legs,
   means for releasably attaching the first crossarm to the crosspiece of the yoke, and
   means for releasably supporting the frame near each end of the second crossarm from the operating table so that the legs of the frame extend over the operating table substantially parallel to its sides.

2. Framework as defined in claim 1 wherein each of the crossarms is centrally disconnectable to separate the frame into two substantially equal pieces.

3. Framework as defined in claim 2 wherein the second crossarm is arched out of the plane defined by the legs and away from an operating table when the framework is supported from the operating table.

4. Framework as defined in claim 3 and wherein said means for supporting the frame near the ends of the second crossarm include a threaded stub projecting from each leg of the frame.

5. Framework as defined in claim 4 wherein said means for supporting the frame near the ends of the second crossarm include a pair of rigid shafts, one each of each of which is threadably connectible to one of said stubs, and the framework includes means for connecting the other end of the shaft to said platform.

6. Framework as defined in claim 5 wherein a siderail extends along each side of the operating table, and said means for supporting the frame near the ends of the second crossarm includes a rigid shaft that is threadably connectible to each of said stubs and a slide at the other end of the shaft that clamps onto one of the siderails.

7. Framework as defined in claim 2 wherein each of said pieces is a metal rod.

8. Framework as defined in claim 1 wherein a seatplate is centrally mounted on said crosspiece, and said means for attaching the first crossarm to the crosspiece includes said seatplate.

9. Framework as defined in claim 1 wherein said crosspiece of the yoke comprises a portion of the first crossarm of the frame.

10. Framework as defined in claim 1 and further comprising a rigid crossbar and means for removably connecting the crossbar across the legs of the frame.

* * * * *

UNITED STATES PATENT AND TRADEMARK OFFICE
CERTIFICATE OF CORRECTION

PATENT NO. : 4,805,599
DATED : February 21, 1989
INVENTOR(S) : Charles D. Ray

It is certified that error appears in the above-identified patent and that said Letters Patent is hereby corrected as shown below:

In column 4, line 56, after the inner, change "facig" to --facing--.

Col. 5, claim 5, after one, change "each" to --end--, in line 9.

Signed and Sealed this

Fourth Day of June, 1991

Attest:

HARRY F. MANBECK, JR.

Attesting Officer

Commissioner of Patents and Trademarks